(12) United States Patent
Breyne et al.

(10) Patent No.: US 6,398,987 B1
(45) Date of Patent: Jun. 4, 2002

(54) NAPHTHOPYRANS HAVING A PERFLUOROALKYL SUBSTITUENT IN POSITION 5, PREPARATION AND COMPOSITIONS AND MATRICES CONTAINING THEM

(75) Inventors: Olivier Breyne; You-Ping Chan; Patrick Jean, all of Lyons (FR)

(73) Assignee: Corning S.A., Avon Cedex (FR)

( * ) Notice: Subject to any disclaimer, the term of this patent is extended or adjusted under 35 U.S.C. 154(b) by 0 days.

(21) Appl. No.: 09/706,121

(22) Filed: Nov. 3, 2000

(30) Foreign Application Priority Data

Nov. 4, 1999 (FR) .............................. 99 13790

(51) Int. Cl.⁷ .................. G02B 5/23; C07D 311/92; G02C 7/10
(52) U.S. Cl. .................. 252/586; 351/163; 549/389; 549/382; 549/383; 549/384; 549/24; 549/25
(58) Field of Search .............. 252/586; 351/163; 549/389, 382, 383, 384, 24, 25

(56) References Cited

U.S. PATENT DOCUMENTS

| | | | |
|---|---|---|---|
| 3,567,605 A | 3/1971 | Becker | 204/158 |
| 3,627,690 A | 12/1971 | Casella et al. | 252/300 |
| 4,826,977 A | 5/1989 | Heller et al. | 544/70 |
| 5,200,116 A | 4/1993 | Heller | 252/586 |
| 5,238,981 A | 8/1993 | Knowles | 524/110 |
| 5,411,679 A | 5/1995 | Kumar | 252/586 |
| 5,420,333 A | 5/1995 | Mori et al. | 560/53 |
| 5,429,774 A | 7/1995 | Kumar | 252/586 |
| 5,451,344 A | 9/1995 | Knowles | 252/586 |
| 5,458,814 A | 10/1995 | Kumar et al. | 455/38 |
| 5,514,817 A | 5/1996 | Knowles | 549/384 |
| 5,548,814 A | 8/1996 | Lorang | 455/38 |
| 5,645,767 A | 7/1997 | Van Gemert | 252/586 |
| 5,651,923 A | 7/1997 | Kumar | 252/586 |
| 5,656,206 A | 8/1997 | Knowles | 252/586 |
| 5,698,141 A | 12/1997 | Kumar | 252/586 |
| 5,783,116 A | 7/1998 | Lin | 252/586 |
| 5,888,432 A | 3/1999 | Chan | 252/586 |

FOREIGN PATENT DOCUMENTS

| | | | |
|---|---|---|---|
| EP | 0 945 451 | 9/1999 | |
| EP | 0 562 915 | 7/2000 | |
| FR | 2 718 447 | 10/1995 | |
| FR | 2 762 845 | 11/1998 | |
| JP | 2000-256347 | * 9/2000 | |
| WO | WO 94 22850 | 10/1994 | |
| WO | W0-A-95 05382 | 2/1995 | ............ 491/4 |
| WO | W0-A-96 14596 | 5/1996 | ............ 311/96 |
| WO | W0-A-97 21698 | 6/1997 | ............ 311/78 |
| WO | W0-A-98 42693 | 10/1998 | |
| WO | W0-A-98 42695 | 10/1998 | ............ 311/78 |
| WO | W0-A-98 57943 | 12/1998 | ............ 311/98 |

OTHER PUBLICATIONS

Edens et al., Mechanism of the Meyer–Schuster Rearrangement, J. Org. Chem., vol. 42, No. 21, 1977, pp. 3403–3408.

* cited by examiner

Primary Examiner—Philip Tucker
(74) Attorney, Agent, or Firm—Angela N. Nwaneri; Peter Rogalskyj

(57) ABSTRACT

The present invention relates to novel compounds of the naphthopyran type which have a perfluoroalkyl group (X) in position 5. These compounds are of formula (I) given below:

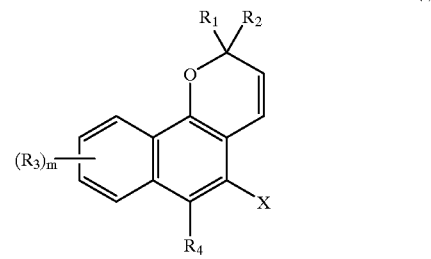

(I)

These compounds (I) possess interesting photochromic properties. The invention also relates to their preparation, their applications as photochromes as well as the compositions and matrices containing them.

27 Claims, No Drawings

NAPHTHOPYRANS HAVING A PERFLUOROALKYL SUBSTITUENT IN POSITION 5, PREPARATION AND COMPOSITIONS AND MATRICES CONTAINING THEM

This application claims the benefit of priority of French Application Serial Number 99 13790 filed Nov. 4, 1999 entitled Naphthopyrans having a Perfluoroalkyl Substituent in Position 5, Preparation and Compositions and Matrices Containing Them of Breyne et al.

The present invention relates to novel naphthopyran-type compounds which have, in particular, photochromic properties. The invention also relates to photochromic compositions and photochromic ophthalmic articles (lenses for example) which contain said naphthopyrans. The invention also covers the preparation of these novel compounds.

The photochromic compounds are capable of changing colour under the influence of a poly- or mono-chromatic light (UV for example) and of returning to their initial colour when the luminous irradiation ceases, or under the influence of temperature and/or a poly- or mono-chromatic light different from the first.

The photochromic compounds find applications in various fields, e.g. for the manufacture of ophthalmic lenses, contact lenses, solar protection glasses, filters, camera optics or photographic apparatus optics or other optical devices and observation devices, glazing, decorative objects, bill elements or even for information storage by optical inscription (coding).

In the field of ophthalmic optics, and in particular the spectacles trade, a photochromic lens which comprises one or more photochromic compounds must have:

- a high transmission in the absence of ultraviolets,
- a low transmission (high colourability) under solar irradiation,
- adapted coloration and discoloration kinetics,
- a tint acceptable to the consumer (grey or brown preferably) with preferably a maintenance of the chosen tint during the coloration and the discoloration of the lens,
- a maintenance of the performances, the properties, within a temperature range of 0–40° C.,
- a significant durability, since these objectives sought after are sophisticated corrective lenses and therefore expensive.

These lens characteristics are in fact determined by the active photochromic compounds which they contain; compounds which must furthermore be perfectly compatible with the organic or inorganic, even hybrid support which constitutes the lens.

Moreover, it is to be noted that obtaining a grey or brown tint may necessitate the use of at least two photochromes of different colours, i.e. having distinct maximal absorption wavelengths in the visible. This combination further imposes other requirements of the photochromic compounds. In particular, the coloration and discoloration kinetics of the (two or more) combined active photochromic compounds must be essentially identical. The same applies for their stability with time and also for their compatibility with a plastic or inorganic support.

Amongst the numerous photochromic compounds described in the prior art, benzopyrans and naphthopyrans may be cited which are described in patents or patent applications: U.S. Pat. No. 3,567,605, U.S. Pat. No. 3,627,690, U.S. Pat. No. 4,826,977, U.S. Pat. No. 5,200,116, U.S. Pat. No. 5,238,981, U.S. Pat. No. 5,411,679, U.S. Pat. No. 5,429,744, U.S. Pat. No. 5,451,344, U.S. Pat. No. 5,458,814, U.S. Pat. No. 5,514,817, U.S. Pat. No. 5,651,923, U.S. Pat. No. 5,645,767, U.S. Pat. No. 5,698,141, U.S. Pat. No. 5,783,116, WO-A-95 05382, FR-A-2,718,447, WO-A-96 14596, WO-A-97 21698, WO-A-98 42693, WO-A-98 42695, and WO-A-98 57943 which are of the reduced formulae below:

Benzopyrans

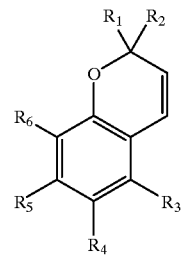

Naphthopyrans

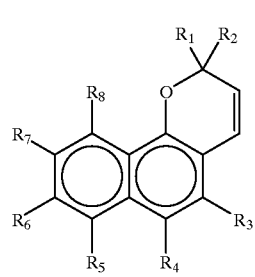

It is well known to the person skilled in the art that the $R_3$ substituents in the α position of the pyran ring enables the discoloration kinetics of the photochromes to be accelerated.

Research disclosure RD 36144 describes naphthopyrans of the following general structure:

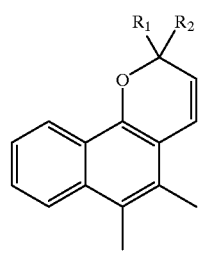

U.S. Pat. No. 5,656,206 describes naphthopyrans of the following general structure:

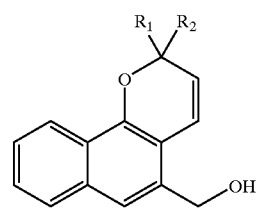

U.S. Pat. No. 5,783,116 describes naphthopyrans of the following general structure:

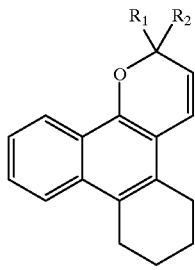

U.S. Pat. No. 5,458,814 describes naphthopyrans of the following general structure:

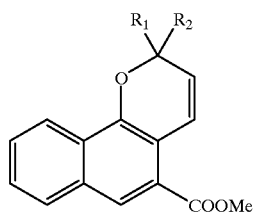

U.S. Pat. No. 5,888,432 of the Applicant describes naphthopyrans of the following general formula:

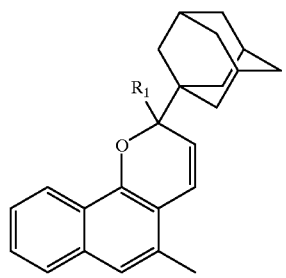

In general, the groups in the $R_3$ position are alkyl groups, ester groups, aryl groups or alkyl groups substituted with a hydroxy.

These compounds claim to satisfy the specifications defined above. In reality, if these compounds really do have one or more of the basic properties sought after, such as a high transmission in the absence of ultraviolets and a high colorability under solar irradiation, none of the compounds described hitherto have the complete combination of the properties sought after which are necessary for the production of satisfactory articles. In particular, none of these compounds is intrinsically grey or brown and the necessity of using an additional photochrome in order to obtain one of these two tints does subsist.

Although the general formula of several patents cited contain "haloalkyl" groups, thus including perfluoroalkyls in the various positions of the naphthyl ring of the naphthopyrans, no access route is suggested and even no perfluoroalkylated product is specifically described. Classically, the access to the naphthopyrans sought after necessitates an intermediate of the <<1-naphthol>> type with a hydrogen in position 2 and a fluoroalkyl in position 3. In the literature, only two products are found which are of this definition, these products are obtained by difficult and costly routes (product A: Taguchi et al. Tetrahedron Lett. 1988, 29, 5765 and product B: U.S. Pat. No. 5,420,333).

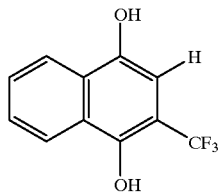

(A : 2-(trifluoromethyl)-1,4-naphthalenediol)

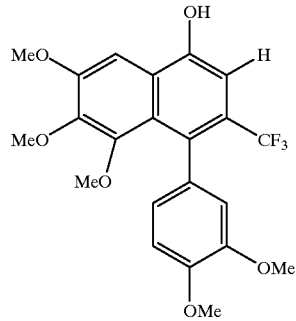

(B : 4-(3,4-dimethoxyphenyl)-5,6,7-trimethoxy-3-(trifluoromethyl)-1-naphthalenol)

In this context, it is to the credit of the inventors:
to have selected compounds of the naphthopyran type, which have a perfluoroalkyl group in the a position of the pyran ring (group X of the formula (I) below) and which possess particularly advantageous photochromic properties. Said compounds possess rapid discoloration kinetics and $\lambda_{max}$ values in the UV and/or the visible which are lower than those of the analogous compounds;
to propose a simple and not very costly access to said compounds, as well in fact as an access route to certain intermediates of naphthol type (compounds of structure II below).

Thus, according to a first of its aspects, the present invention relates to compounds of the following formula (I):

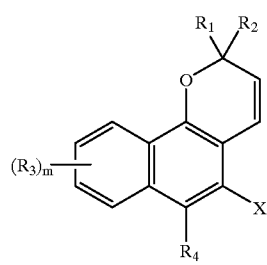

(I)

in which:
X is a linear or branched perfluoroalkyl comprising 1 to 6 carbon atoms;
$R_1$ and $R_2$, which are identical or different, independently represent:
hydrogen,
a linear or branched alkyl group comprising 1 to 12 carbon atoms,
a cycloalkyl group comprising 3 to 12 carbon atoms,
an aryl or heteroaryl group comprising in its basic structure 6 to 24 carbon atoms or 4 to 24 carbon atoms respectively and at least one heteroatom selected from sulphur, oxygen and nitrogen; said basic structure being optionally substituted with at least one substituent selected from the whole of the substituents given below:
a halogen, and notably fluorine, chlorine and bromine,
a hydroxy,
a linear or branched alkyl group comprising 1 to 12 carbon atoms,
a linear or branched alkoxy group comprising 1 to 12 carbon atoms,
a haloalkyl or haloalkoxy group corresponding to the ($C_1$–$C_{12}$) alkyl or alkoxy groups above respectively which are substituted with at least one halogen atom, and notably a fluoroalkyl group of this type,
a phenoxy or naphthoxy group optionally substituted with at least one linear or branched alkyl or alkoxy group comprising 1 to 12 carbon atoms,
a linear or branched alkenyl group comprising 2 to 12 carbon atoms, and notably a vinyl group or an allyl group,
an —$NH_2$ group,
an —NHR group, R representing a linear or branched alkyl group comprising 1 to 6 carbon atoms, or a phenyl group optionally substituted with at least one linear or branched alkyl group comprising 1 to 6 carbon atoms,
a

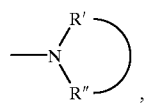

group, R' and R", which are identical or different, representing independently a linear or branched alkyl group comprising 1 to 6 carbon atoms, or a phenyl group optionally substituted with at least one linear or branched alkyl group comprising 1 to 6 carbon atoms, or representing together with the nitrogen atom to which they are bound a 5- to 7-membered ring which can comprise at least one other heteroatom selected from oxygen, sulphur and nitrogen, said nitrogen being optionally substituted with an R'" group, which is a linear or branched alkyl group comprising 1 to 6 carbon atoms,
a methacryloyl group or an acryloyl group,
an aralkyl or heteroaralkyl group, the alkyl group of which, which is linear or branched, comprises 1 to 4 carbon atoms and the aryl part or heteroaryl part of which has the same definition as that given supra for the aryl and heteroaryl group;
or
said two substituents $R_1$ and $R_2$ together form an adamantyl, norbornyl, fluorenylidene, di($C_1$–$C_6$) alkylanthracenylidene or spiro($C_5$–$C_6$) cycloalkylanthracenylidene group; said group being optionally substituted with at least one of the substituents listed above for $R_1$, $R_2$: an aryl or heteroaryl group;
$R_3$, which are identical or different, independently represent:
a halogen, and notably fluorine, chlorine or bromine,
a hydroxy,
a linear or branched alkyl group comprising 1 to 12 carbon atoms (advantageously 1 to 6 carbon atoms), a cycloalkyl group comprising 3 to 12 carbon atoms,
a linear or branched alkoxy group comprising 1 to 12 carbon atoms (advantageously 1 to 6 carbon atoms),
a haloalkyl, halocycloalkyl, or haloalkoxy group corresponding to the alkyl, cycloalkyl, alkoxy groups above respectively, which are substituted with at least one halogen atom, notably selected from fluorine, chlorine and bromine,
an aryl or heteroaryl group having the same definition as that given supra for $R_1$, $R_2$,
an aralkyl or heteroaralkyl group, the alkyl group, which is linear or branched, comprises 1 to 4 carbon atoms, and the aryl and heteroaryl groups having the same definitions as those given supra for $R_1$, $R_2$,
a phenoxy or naphthoxy group optionally substituted with at least one linear or branched alkyl or alkoxy group comprising 1 to 12 carbon atoms,
an amine or amide group: —$NH_2$, —NHR, —$CONH_2$, —CONHR,

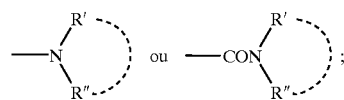

R, R', R" having their respective definitions given supra for the amine substituents of the values $R_1$, $R_2$: aryl or heteroaryl,
an —$OCOR_6$ or —$COOR_6$ group, $R_6$ representing a linear or branched alkyl group comprising 1 to 6 carbon atoms, or a cycloalkyl group comprising 3 to 6 carbon atoms, or a phenyl group, optionally substituted with at least one of the substituents listed above for the values of $R_1$, $R_2$: aryl or heteroaryl;
or
at least two of the adjacent $R_3$ groups together form an aromatic or non-aromatic cyclic group having one or two annelated rings which can comprise at least one heteroatom selected from the group consisting of: oxygen, sulphur or nitrogen; this or these rings, independently 5- to 7-membered aromatic or non-aromatic, being able to comprise at least one substituent selected from a group as defined above, as a substituent, of the basic structure of the aryl or heteroaryl group representing $R_1$ or $R_2$;
m is an integer of 0 to 4;
$R_4$ represents a hydrogen, a hydroxy, a linear or branched allyl comprising 1 to 12 carbon atoms, a linear or branched alkoxy comprising 1 to 12 carbon atoms, an ester of formula $OCOR_6$ defined supra, an aryl or heteroaryl as defined supra for $R_1$ or $R_2$.

The person skilled in the art will obviously have understood that the branched alkyl, alkoxy and alkenyl groups as defined above comprise a number of carbons which is sufficient to be able to be branched (more than 3, more than 3 and more than 4 carbon atoms, respectively).

The compounds of the invention—naphthopyrans of formula (I)—possess a strong colorability, even at 40° C., combined with discoloration kinetics which are adapted to the applications sought after. The colours, which are easily accessible, vary from yellow to pink.

Amongst said compounds of the invention, preferred are:
with reference to the X substituent, those which are of formula (I) in which X is a —$CF_3$ or —$C_2F_5$ group;
with reference to the $R_1$ and $R_2$ substituents, those which are of formula (I) in which $R_1$, $R_2$ are identical or different and represent independently optionally substituted aryl or heteroaryl groups the basic structure of which is selected from the group consisting of phenyl, naphthyl, biphenyl, pyridyl, furyl, benzofuryl, dibenzofuryl, N—($C_1$–$C_6$)alkylcarbazole, thienyl, benzothienyl, dibenzothienyl and julolidinyl groups; $R_1$ and/or $R_2$ representing, advantageously, a para-substituted phenyl group;

or $R_1$ and $R_2$ together form an adamantyl or norbomyl group.

Amongst said compounds of the invention, with reference to the $R_3$ substituents, those which belong to one or the other of the sub-families below are distinguished:

the compounds of formula (I), without an $R_3$ substituent (m=0);

the compounds of formula (I), with independent $R_3$ substituents;

the compounds of formula (I), at least two adjacent $R_3$ groups of which together form an aromatic or non-aromatic cyclic group having one or two annelated rings which can comprise at least one heteroatom selected from the group consisting of: oxygen, sulphur or nitrogen; this or these rings, independently 5- to 7-membered aromatic or non-aromatic, being able to comprise at least one substituent selected from a group as defined above, as a substituent, of the basic structure of the aryl or heteroaryl group representing $R_1$ or $R_2$. Phenyl, benzofuran, benzothienyl, and indene rings are particularly preferred.

Those which belong to the first, and more particularly those which belong to the third of these families, are preferred.

According to a second of its aspects, the present invention relates to a method of preparing compounds of formula (I), characterised in that it consists, essentially, in carrying out a condensation:

of an intermediate product of formula (II) below

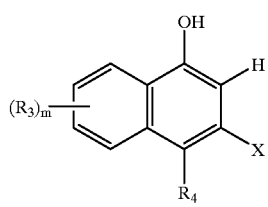

(II)

in which X, $R_3$, $R_4$ and m are as defined above with reference to formula (I), with a derivative of propargylic alcohol, having formula (III) below:

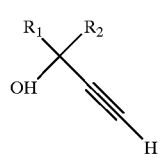

(III)

in which $R_1$ and $R_2$ are as defined supra with reference to formula (I);

the condensation (II)/(III) being carried out advantageously in the presence of a catalyst, this catalyst being preferably selected from the group comprising para-toluenesulphonic acid, dodecylsulphonic acid or bromoacetic acid;

or with an aldehyde derivative, having formula (III') below:

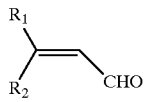

(III')

in which $R_1$ and $R_2$ are as defined supra with reference to formula (I);

the condensation (II)/(III') being carried out, advantageously, in the presence of a metallic complex, preferably a complex of titanium, titanium (IV) ethoxide being particularly preferred.

In practice, the condensation reaction between compounds (II) and (III) or (II) and (III') can take place in solvents such as toluene, xylene or tetrahydrofuran, to which appropriate catalysts are optionally added (vide U.S. Pat. No. 5,783,116). For more details on the condensation of compounds (II) and (III'), reference may be made to the EP-A-0 562 915 patent application.

The compounds of formula (III) are known to the person skilled in the art and are obtained from the corresponding ketone according to a method described notably in the WO-A-96 14596 patent application. The ketone is itself commercial or is prepared according to the known methods such as the Friedel Crafts method (cf WO-A-96 14596 and cited references).

Aldehydes (III'), which are derivatives of (III), are obtained by rearrangement in an acid medium (cf. *J. Org. Chem.*, 1977, 42, 3403).

The compounds of formula (II) above are novel with the exception of 2-(trifluoromethyl)-1,4-naphthalenediol and 4-(3,4-dimethoxyphenyl)-5,6,7-trimethoxy-3-(trifluoromethyl)-1-naphthalenol described above. They can be obtained according to a synthesis scheme the various steps of which are adaptations of known methods.

Thus, other objects of the present invention are:

the method of preparing said naphthopyrans of formula (I) from compounds of formula (II) (vide supra);

said compounds of formula (II) with the exception of 2-(trifluoromethyl)-1,4-naphthalenediol and 4-(3,4-dimethoxyphenyl)-5,6,7-trimethoxy-3-(trifluoromethyl)-1-naphthalenol; and a method of obtaining said compounds of formula (II).

Said method of synthesising compounds of formula (II) comprises:

for the compounds of formula (II) in which $R_4$ represents a hydrogen, a linear or branched alkyl having 1 to 12 carbon atoms or an aryl or heteroaryl as defined above for $R_1$ or $R_2$, cyclising compounds of formula (IV), according to:

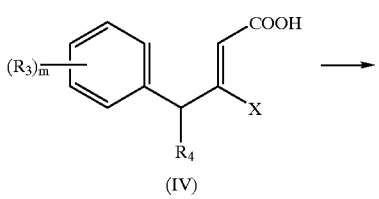

(IV)

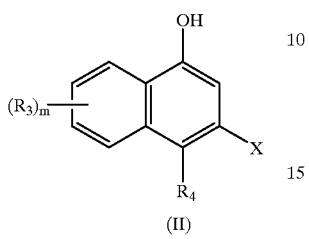

(II)

This cyclisation is carried out by heating in acetic anhydride in the presence of sodium acetate, followed by a hydrolysis in basic medium. This type of reaction is described for example by Regaila et al. in Indian. J. Chem. 1982, 21B, 658–661.

The compounds of formula (IV) can be obtained by a basic hydrolysis of the corresponding esters, which are themselves obtained according to the methods described by Coe et al. in J. Fluor. Chem. 1997, 113–118 and Shen et al. in J. Org. Chem. 1993, 58, 4564–4566;

for the compounds of formula (II) in which $R_4$=OH, a linear or branched alkoxy group having 1 to 12 carbon atoms, an ester of formula $OCOR_6$, preparing said compounds of formula (II) in which $R_4$=OH, followed if necessary by alkylating or esterifyng the hydroxy function; said preparation of said compounds of formula (II) in which $R_4$=OH advantageously consisting of reducing compounds of formula (VI), according to:

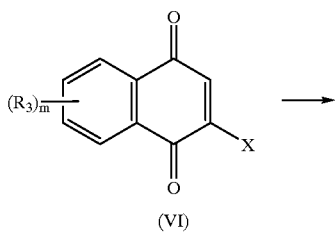

(VI)

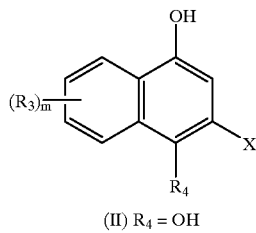

(II) $R_4$ = OH

This reduction is described by Taguchi et al. in Tetrahedron Lett. 1988, 29, 5765–5766.

The compounds of formula (I) are prepared from the intermediates of formula (II) as indicated above.

The compounds of formula (II) and their preparation constitute the third aspect of the present invention.

According to a fourth of its aspects, the object of the invention is (co)polymer(s) and/or reticulate(s) obtained by polymerising and/or cross-linking and/or grafting at least one compound (I) as defined above. The compounds (I) according to the invention can be per se (co)monomers and/or be comprised in (co)polymerisable and/or cross-linkable (co)monomers. The (co)polymers and/or reticulates thus obtained can constitute photochromic matrices such as those presented infra.

According to a fifth of its aspects, the present invention relates to the use of said compounds of formula (I) of the invention as photochromic agents. Another object of the invention is, therefore:

firstly, novel photochromic compounds which are constituted by the naphthopyran or phenanthropyran derivatives such as defined above, taken alone or in a mixture of themselves and/or with at least one other photochromic compound of another type and/or with at least one non-photochromic colouring agent;

secondly, novel photochromic compositions which comprise at least one compound (I) as defined above, and/or at least one linear or cross-linked (co)polymer containing at least one compound (I) according to the invention in its structure. Such photochromic compositions can contain at least one other photochromic compound, of another type and/or at least one non-photochromic colouring agent and/or at least one stabilising agent. These photochromic compounds of another type, non-photochromic colouring agents, and stabilising agents are prior art products known to the person skilled in the art.

Within the context of the present invention, combinations of photochromic compounds of the invention and/or combinations of photochromic compounds of the invention and photochromic compounds of another type according to the prior art are particularly recommended; such combinations being interesting in that they are suitable for generating grey or brown tints, which are desired by the public in applications such as ophthalmic spectacles or solar spectacles. These additional photochromic compounds can be those known to the person skilled in the art and described in the literature, e.g. chromenes (U.S. Pat. No. 3,567,605, U.S. Pat. No. 5,238,981, WO-A-94 22850, EP-A-0 562 915), spiropyrans or naphthospiropyrans (U.S. Pat. No. 5,238,981) and spiroxazines (Crano et al., "Applied Photochromic Polymer Systems", Ed. Blackie & Son Ltd, 1992, chapter 2).

Said compositions according to the invention can also comprise:

non-photochromic coloring agents which enable adjusting the tint, and/or one or more stabilising agents, such as an anti-oxidising agent for example, and/or one or more anti-UV, and/or one or more anti-radicals, and/or one or more photochromic excited state deactivators.

These additives can notably enable improving the durability of said compositions.

The compounds of the invention envisaged within the context of their photochromic applications can be used in solution. Thus, a photochromic solution can be obtained by dissolving at least one of said compounds in an organic solvent such as toluene, dichloromethane, tetrahydrofuran or ethanol. The solutions obtained are in general colourless and transparent. When exposed to sunlight, they develop a strong coloration and regain the colourless state when they are placed in an area of less exposure to the sun's rays or, in other words, when they are no longer subjected to UV. In general, a very low concentration of product (of the order of 0.01 to 5% by weight) is sufficient to obtain an intense coloration.

The compounds according to the invention are furthermore compatible with support matrices of organic polymer or of inorganic material, in a form included in said matrices as well as in the form of a coating of said matrices.

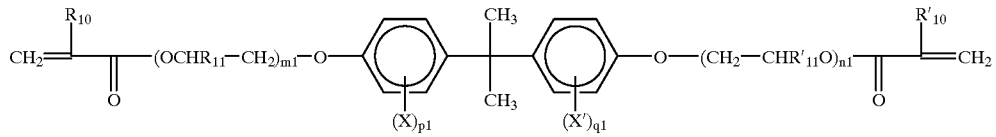

Also, within the context of the fifth aspect of the invention in relation to the photochromic applications, the object of the invention is a matrix which comprises:
- at least one compound (I), as defined supra;
- and/or at least one (co)polymer and/or reticulate, as defined supra;
- and/or at least one composition, as presented above.

The most interesting applications of the compounds of the invention are in fact those in which the photochrome is dispersed uniformly within or on the surface of a matrix formed by a polymer and/or copolymer and/or mixture of (co)polymers.

Following the example of their behaviour in solution, the compounds (I), included in a polymer matrix are colourless or slightly coloured in the initial state and rapidly develop an intense coloration under a TV light (365 nm) or under a light source of the solar type. Finally, they regain their initial coloration once the irradiation ceases.

The methods of implementation which can be envisaged in order to obtain such a matrix are very varied. Amongst those known to the person skilled in the art, the diffusion in the (co)polymer, from a suspension or solution of the photochrome, in a silicone oil, in an aliphatic or aromatic hydrocarbon, or in a glycol, or from another polymer matrix, can be cited for example. The diffusion is commonly carried out at a temperature of 50 to 200° C. for a period of time of 15 minutes to several hours, according to the nature of the polymer matrix. Another implementation technique consists in mixing the photochrome in a formulation of polymerisable materials, depositing this mixture on a surface or in a mould, and then carrying out the copolymerisation. These implementation techniques, and others, are described in the article by Crano et al. "Spiroxazines and their use in photochromic lenses" published in Applied Photochromic Polymer Systems, Ed. Blackie and Son Ltd—1992.

The following products may be mentioned as examples of preferred polymer materials for forming matrices which are useful in optical applications of the photochromic compounds according to the invention:
- those obtained from alkyl, cycloalkyl, (poly or oligo) ethylene glycol, aryl or arylalkyl mono-, di- tri- or tetraacrylate or mono-, di-, tri- or tetramethacrylate, which is optionally halogenated or which comprises at least one ether and/or ester and/or carbonate and/or carbamate and/or thiocarbamate and/or urea and/or amide group,
- polystyrene, polyether, polyester, polycarbonate (e.g. bisphenol-A polycarbonate, diallyl diethylene glycol polycarbonate), polycarbamate, polyepoxy, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate or polyvinylbutyral,
- those obtained from difunctional monomers having the formula below:

in which:
- $R_{10}$, $R'_{10}$, $R_{11}$ and $R'_{11}$ are identical or different and represent independently a hydrogen or a methyl group;
- $m_1$ and $n_1$ are, independently, integers between 0 and 4 (inclusive); and are advantageously independently equal to 1 or 2;
- X and X', which are identical or different, are a halogen and represent, preferably, a chlorine and/or a bromine;
- $p_1$ and $q_1$ are, independently, integers between 0 and 4 (inclusive);
- copolymers of at least two types of copolymerisable monomers selected from the precursor monomers of the polymers listed supra, and preferably those belonging to the groups comprising: (meth)acrylic monomers, vinylic monomers, allylic monomers, and mixtures thereof.

In a particularly preferred manner, the photochromes of the invention are used with resins which have a nanobiphasic structure and which are obtained by copolymerising at least two different, specific difunctional monomers. Such resins have been described by the Applicant in the French patent Application FR-A-2,762,845.

The amount of photochrome used in the (co)polymer matrix depends upon the degree of darkening desired. Usually, between 0.001 and 20% by weight of it is used.

Still according to the fifth of its aspects in relation to the applications of the compounds (I) as photochromes, another object of the present invention is ophthalmic articles, such as ophthalmic or solar spectacle articles, comprising:
- at least one compound (I) according to the invention,
- and/or at least one (co)polymer and/or reticulate formed, at least in part, from compound(s) of the invention,
- and/or at least one photochromic composition as defined above,
- and/or at least one matrix (as defined supra), of an organic polymer material or of an inorganic material, or even of a hybrid inorganic-organic material, said matrix initially optionally comprising at least one compound of the invention.

In practice, the articles which are more particularly covered by the present invention are ophthalmic lenses or photochromic solar lenses, glazing (windows for buildings, for locomotion engines, automobile vehicles), optical devices, decorative articles, solar protection articles, information storage, . . .

The present invention is illustrated by the Examples which follow, of synthesis and of photochromic validation, of compounds of the invention. The compounds of the invention are compared to prior art compounds $C_1$ and $C_2$.

EXAMPLES

Example 1

SYNTHESIS OF COMPOUND (1)

The synthesis of compound (1) was carried out according to the route described below.

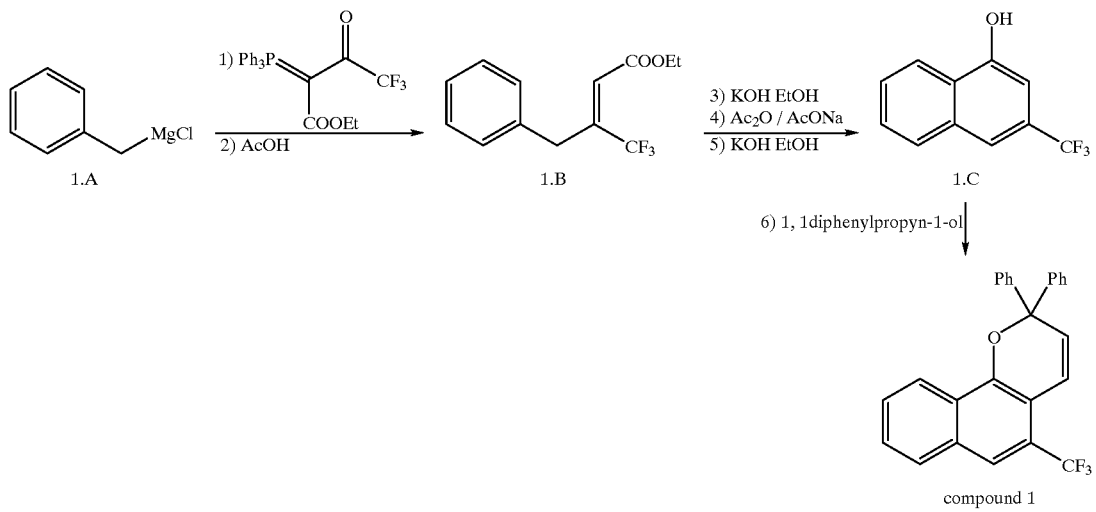

Steps 1 and 2:

The trifluoromethyl ester derivative (1.B) was prepared according to the procedure described by Shen et al. (J. Org. Chem. 1993, 58, 4564–4566) in starting from the Grignard reagent of benzyl chloride.

Step 3:

6 g of product 1.B were heated under reflux for 2 hours in ethanol in the presence of 3 g of KOH. After neutralisation, 4.2 g of the corresponding acid were recovered.

Steps 4 and 5:

The acid from the preceding step was dissolved in 20 ml of acetic anhydride and 2 g of sodium acetate were added thereto. The mixture was heated under reflux for 4 hours. 3 g of 1.C were recovered after basic hydrolysis and chromatography on a silica column.

Step 6:

The following mixture: 0.9 g of the product of the preceding step, 1 g of 1,1-diphenyl-propyn-1-ol in 10 ml of xylene in the presence of a catalytic amount of dodecylsulphonic acid were heated under reflux for 30 minutes in a 50 ml reactor. The product was then purified by chromatography on silica. About 600 mg of compound 1 were obtained. Its structure was confirmed by NMR spectroscopy.

Example 2

SYNTHESIS OF COMPOUND (2)

The synthesis of compound (2) was carried out according to the same procedure as for Example 1, in starting with the Grignard reagent from 2-bromomethylnaphtalene.

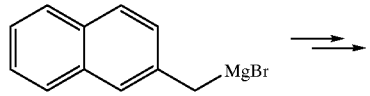

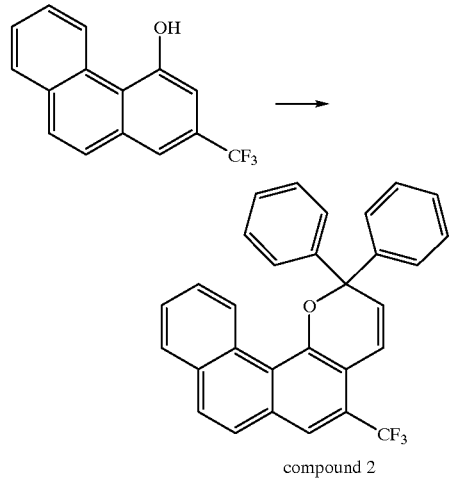

compound 2

Example 3

SYNTHESIS OF COMPOUND (3)

The synthesis of compound (3) was carried out according to the same procedure as above except that 1-(para-trifluoromethylphenyl)-1-phenyl-propyn-1-ol was used in step 6.

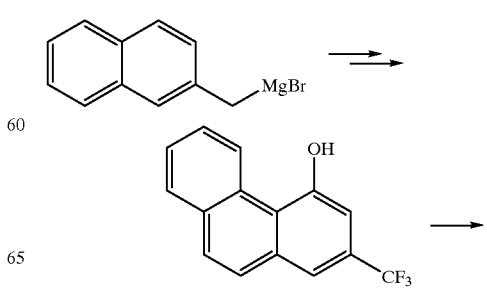

-continued

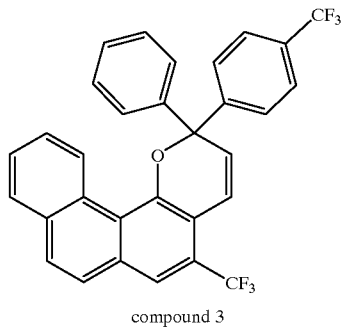

compound 3

Example 4

SYNTHESIS OF COMPOUND (4)

The synthesis of compound (4) was carried out according to the same method as for Example 1 in starting with chloromethyl dibenzofuran in step 1 and in using 1-(para-trifluoromethylphenyl)-1-phenyl-propyn-1-ol in step 6.

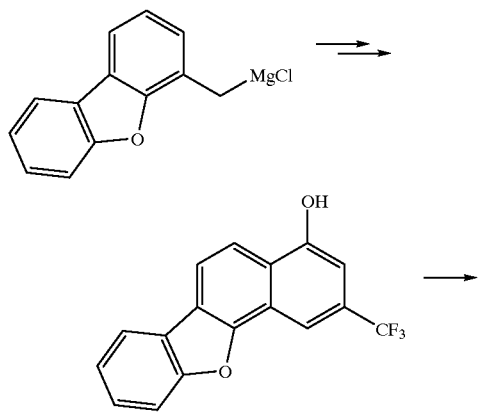

-continued

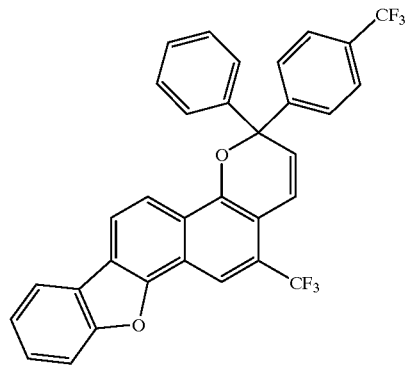

compound 4

Example 5

COMPOUNDS C1, C2

Compounds C1 and C2 were synthesised according to the procedures indicated in the Research Disclosure RD 36144 and U.S. Pat. No. 5,656,206, respectively.

Example 6

The photochromic properties of said compounds (1), (2), (3), (4), C1 and C2 were evaluated.

Said compounds were dissolved, at the rate of 5 mg in 50 ml of THF. The UV-visible absorptions (optical path of 1 cm) were then measured before and after exposure to a UV source at 365 nm. The observation of the tints and the intensities developed was done by placing the solutions in the sun or before a solar simulator. The properties of these compounds are given in the Table below.

| COMPOUND | STRUCTURE | λmax* | T½** |
|---|---|---|---|
| 1 | 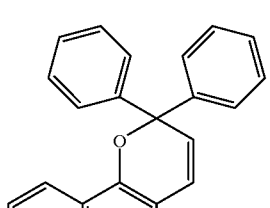 | 456 nm | 19 s |

-continued
| COMPOUND | STRUCTURE | λmax* | T½** |
|---|---|---|---|
| C1 | 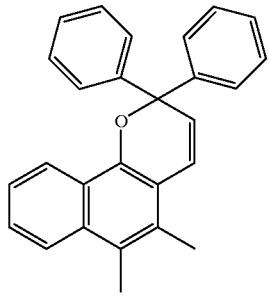 | 469 nm | 250 s |
| C2 | 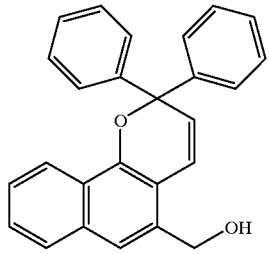 | 466 nm | 250 s |
| 2 | 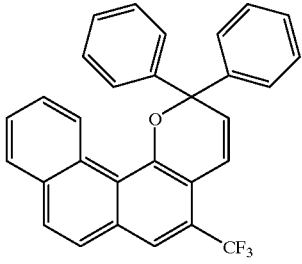 | 447 nm | 5 s |
| 3 | 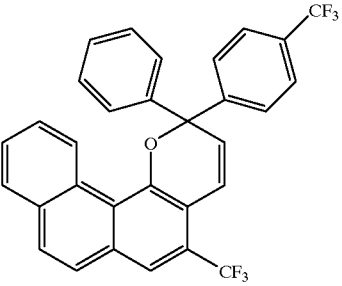 | 445 nm | 13 s |

-continued

| COMPOUND | STRUCTURE | λmax* | T½** |
|---|---|---|---|
| 4 | 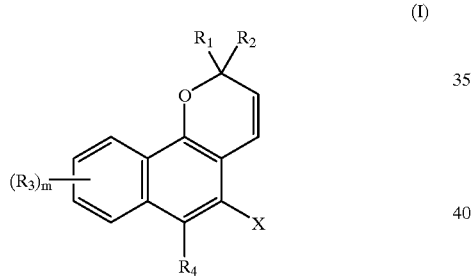 | 452 nm | 13 s |

*λmax: maximum of the longest wavelength band of the compound after exposure.
**T½: decoloration time corresponding to 50% decrease of absorption at the λmax at 21° C.

The observation of the solutions of these compounds in the presence of sun's rays or UV rays shows that the compounds of the invention have λmax's which are shifted towards shorter wavelengths (hypsochromic shift). This can be seen by comparing 1 to C1 and C2. A notable influence upon the discoloration kinetics was also noted.

What is claimed is:

1. A compound having the following formula (I):

(I)

in which:
X is a linear or branched perfluoroalkyl comprising 1 to 6 carbon atoms;
$R_1$ and $R_2$, which are identical or different, independently represent:
hydrogen,
a linear or branched alkyl group comprising 1 to 12 carbon atoms,
a cycloalkyl group comprising 3 to 12 carbon atoms,
an aryl group comprising in its basic structure 6 to 24 carbon atoms or a heteroaryl group comprising in its basic structure 4 to 24 carbon atoms and at least one heteroatom selected from sulfur, oxygen and nitrogen, said aryl or heteroaryl group's basic structure being optionally substituted with at least one substituent selected from the group consisting of:
a halogen,
a hydroxy group,
a linear or branched alkyl group comprising 1 to 12 carbon atoms,
a linear or branched alkoxy group comprising 1 to 12 carbon atoms,
a haloalkyl or haloalkoxy group corresponding respectively to the ($C_1$–$C_{12}$) alkyl or alkoxy groups above which are substituted with at least one halogen atom,
a phenoxy or naphthoxy group optionally substituted with at least one linear or branched alkyl or alkoxy group comprising 1 to 12 carbon atoms,
a linear or branched alkenyl group comprising 2 to 12 carbon atoms,
an —$NH_2$ group,
an —NHR group, R representing a linear or branched alkyl group comprising 1 to 6 carbon atoms, or a phenyl group optionally substituted with at least one linear or branched alkyl group comprising 1 to 6 carbon atoms,
a

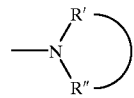

group wherein R' and R", which are identical or different, independently represent a linear or branched alkyl group comprising 1 to 6 carbon atoms or a phenyl group optionally substituted with at least one linear or branched alkyl group comprising 1 to 6 carbon atoms or wherein R' and R" represent together with the nitrogen atom to which they are bound a 5- to 7-membered ring which optionally comprises at least one other heteroatom selected from oxygen, sulfur, and nitrogen, said nitrogen being optionally substituted with an R'" group, which is a linear or branched alkyl group comprising 1 to 6 carbon atoms, and
a methacryloyl group or an acryloyl group, or
an aralkyl or heteroaralkyl group, the alkyl part of which is linear or branched and comprises 1 to 4 carbon atoms and the aryl part or heteroaryl part of which has the same definition as that given above for the aryl and or heteroaryl group;
or
said two substituents $R_1$ and $R_2$ together form an adamantyl, norbornyl, fluorenylidene, di($C_1$–$C_6$) alkylanthracenylidene, or spiro($C_5$–$C_6$)

cycloalkylanthracenylidene group, said group being optionally substituted with at least one substituent selected from the group consisting of:
a halogen,
a hydroxy group,
a linear or branched alkyl group comprising 1 to 12 carbon atoms,
a linear or branched alkoxy group comprising 1 to 12 carbon atoms,
a haloalkyl or haloalkoxy group corresponding to the $(C_1-C_{12})$ alkyl or alkoxy groups above, respectively, which are substituted with at least one halogen atom,
a linear or branched alkenyl group comprising 2 to 12 carbon atoms,
an —$NH_2$ group,
an —NHR group, wherein R represents a linear or branched alkyl group comprising 1 to 6 carbon atoms,
a

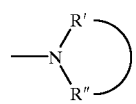

group, wherein R' and R", which are identical or different, represent, independently, a linear or branched alkyl group comprising 1 to 6 carbon atoms or R' and R", together with the nitrogen atom to which they are bound, represent a 5- to 7-membered ring which optionally comprises at least one other heteroatom selected from oxygen, sulphur, and nitrogen, said nitrogen being optionally substituted with an R''' group, which is a linear or branched alkyl group comprising 1 to 6 carbon atoms, and
a methacryloyl group or an acryloyl group;
$R_3$, which are identical or different, represent, independently:
a halogen,
a hydroxy,
a linear or branched alkyl group comprising 1 to 12 carbon atoms,
a cycloalkyl group comprising 3 to 12 carbon atoms,
a linear or branched alkoxy group comprising 1 to 12 carbon atoms,
a haloalkyl, halocycloalkyl, or haloalkoxy group corresponding respectively to the alkyl, cycloalkyl, and alkoxy groups above, which are substituted with at least one halogen atom,
an aryl or heteroaryl group having the same definition as that given above for $R_1$, $R_2$,
an aralkyl or heteroaralkyl group, the alkyl part of which is linear or branched and comprises 1 to 4 carbon atoms and the aryl and heteroaryl part of which has the same definitions as those given above for $R_1$, $R_2$,
a phenoxy or naphthoxy group optionally substituted with at least one linear or branched alkyl or alkoxy group comprising 1 to 12 carbon atoms,
an amine or amide group: —$NH_2$, —NHR, —$CONH_2$, —CONHR,

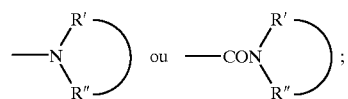

wherein R represents a linear or branched alkyl group comprising 1 to 6 carbon atoms and wherein R' and R", which are identical or different, represent, independently, a linear or branched alkyl group comprising 1 to 6 carbon atoms or R' and R", together with the nitrogen atom to which they are bound, represent a 5- to 7-membered ring which optionally comprises at least one other heteroatom selected from oxygen, sulphur, and nitrogen, said nitrogen being optionally substituted with an R''' group, which is a linear or branched alkyl group comprising 1 to 6 carbon atoms,
an —$OCOR_6$ or —$COOR_6$ group, $R_6$ representing a linear or branched alkyl group comprising 1 to 6 carbon atoms, a cycloalkyl group comprising 3 to 6 carbon atoms, or a phenyl group, optionally substituted with at least one substituent selected from the group consisting of:
a halogen,
a hydroxy group,
a linear or branched alkyl group comprising 1 to 12 carbon atoms,
a linear or branched alkoxy group comprising 1 to 12 carbon atoms,
a haloalkyl or haloalkoxy group corresponding to the $(C_1-C_{12})$ alkyl or alkoxy groups above, respectively, which are substituted with at least one halogen atom,
a linear or branched alkenyl group comprising 2 to 12 carbon atoms,
an —$NH_2$ group,
an —NHR group, wherein R represents a linear or branched alkyl group comprising 1 to 6 carbon atoms,
a

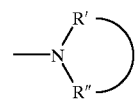

group, wherein R' and R", which are identical or different, represent, independently, a linear or branched alkyl group comprising 1 to 6 carbon atoms or R' and R", together with the nitrogen atom to which they are bound, represent a 5- to 7-membered ring which optionally comprises at least one other heteroatom selected from oxygen, sulphur, and nitrogen, said nitrogen being optionally substituted with an R''' group, which is a linear or branched alkyl group comprising 1 to 6 carbon atoms, and
a methacryloyl group or an acryloyl group;
or
at least two of the adjacent $R_3$ groups together form an aromatic or non-aromatic cyclic group having one or two annelated rings, optionally comprising at least one heteroatom selected from the group consisting of oxygen, sulfur, and nitrogen, this or these annelated rings being independently 5- to 7-membered aromatic or non-aromatic rings and being optionally substituted with at least one substituent selected from those having the definition given above for the aryl or heteroaryl groups representing $R_1$ or $R_2$;

m is an integer of 0 to 4; and $R_4$ represents a hydrogen, a hydroxy, a linear or branched alkyl comprising 1 to 12 carbon atoms, a linear or branched alkoxy comprising 1 to 12 carbon atoms, an aryl or heteroaryl as defined above for $R_1$ or $R_2$, or an ester of formula $OCOR_6$, where $R_6$ is as defined above.

2. A compound according to claim 1, wherein X is a $CF_3$ or $C_2F_5$ group.

3. A compound according to claim 1, wherein:

$R_1$ and $R_2$ are identical or different and independently represent optionally substituted aryl or heteroaryl groups, the basic structure of which is selected from the group consisting of phenyl, naphthyl, biphenyl, pyridyl, finyl, benzofuryl, dibenzofuryl, N-($C_1$–$C_6$) alkylcarbazole, thienyl, benzothienyl, dibenzothienyl, and julolidinyl groups; or $R_1$ and $R_2$ together form an adamantyl or norbomyl group.

4. A compound according to claim 1, wherein at least one of $R_1$ and $R_2$ represents a para-substituted phenyl group.

5. A compound according to claim 1, wherein at least two adjacent $R_3$ groups together form an aromatic or non-aromatic cyclic group having one or two annelated rings, which rings are 5- to 7-membered, which rings can optionally contain at least one heteroatom selected from the group consisting of oxygen, sulfur, and nitrogen, and which rings are optionally substituted with at least one substituent selected from those having the definition given in claim 1 for the aryl or heteroaryl group representing $R_1$ or $R_2$.

6. A method of preparing compounds according to claim 1, said method comprising:

condensing a compound of formula (II):

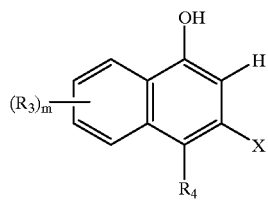

(II)

in which X, $R_3$, $R_4$, and m are as defined as in claim 1, with a dertivative of a propargylic alcohol of formula (III):

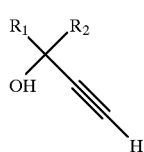

(III)

in which $R_1$ and $R_2$ are as defined in claim 1, the (II)/(III) condensation being optionally carried out in the presence of a catalyst selected from the group consisting of para-toluenesulfonic acid, dodecylsulfonic acid, and bromoacetic acid; or with an aldehyde derivative, having formula (III') below:

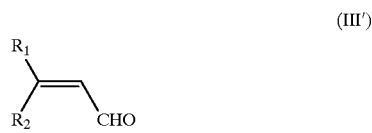

(III')

in which $R_1$ and $R_2$ are defined as in claim 1, the (II)/(III') condensation being optionally carried out in the presence of a metallic complex of titanium.

7. A (co)polymer and/or reticulate obtained by polymerizing and/or cross-linking and/or grafting at least one monomer comprising at least one compound according to claim 1.

8. A photochromic compound which is constituted by a compound according to claim 1, or by a mixture of at least two compounds according to claim 1, or by a mixture of at least one compound according to claim 1 and at least one other photochromic compound of a different type and/or at least one non-photochromic coloring agent.

9. A photochromic composition which comprises:

at least one compound according to claim 1, and/or at least one linear or crosslinked (co)polymer which contains, in its structure, at least one compound according to claim 1, and optionally, at least one other photochromic compound of a different type and/or at least one non-photochromic coloring agent and/or at least one stabilizing agent.

10. A (co)polymer matrix, characterized in that it comprises:

at least one compound according to claim 1.

11. A (co)polymer matrix according to claim 10, wherein the (co)polymer is selected from the group consisting of:

an alkyl, cycloalkyl, (poly or oligo)ethylene glycol, aryl or arylalkyl mono-, di-, tri-, or tetra-acrylate or mono-, di-, tri- or tetra-methacrylate which is optionally halogenated or which optionally comprises at least one ether and/or ester and/or carbonate and/or carbamate and/or thiocarbamate and/or urea and/or amide group, a polystyrene, polyether, polyester, polycarbonate, polycarbamate, polyepoxide, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate, or polyvinylbutyral, a (co)polymer obtained from a difunctional monomer of the following formula:

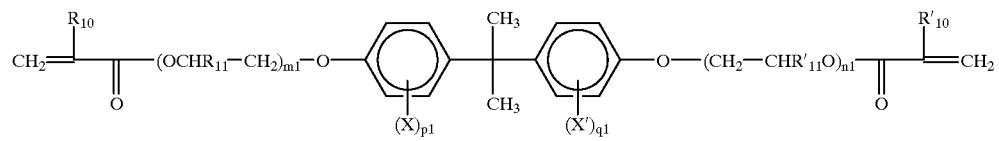

in which:
  $R_{10}$, $R'_{10}$, $R_{11}$ and $R'_{11}$ are identical or different and independently are a hydrogen or a methyl group,
  $m_1$ and $n_1$ independently are integers between 0 and 4 inclusive,
  X and X', which are identical or different, are a halogen, and
  $p_1$ and $q_1$ independently are integers between 0 and 4 inclusive;
a copolymer of at least two types of copolymerizable monomers selected from the monomers which are precursors of the polymers listed above; and
combinations thereof.

12. A (co)polymer matrix which comprises:
  at least one photochromic composition according to claim 9.

13. A (co)polymer matrix according to claim 12, wherein the (co)polymer is selected from the group consisting of:

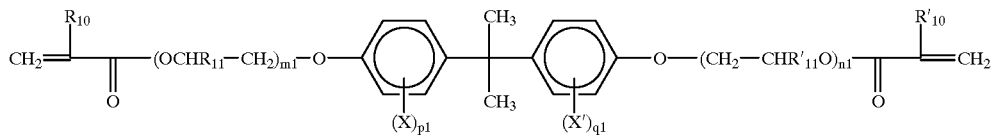

an alkyl, cycloalkyl, (poly or oligo)ethylene glycol, aryl or arylalkyl mono-, di-, tri-, or tetra-acrylate or mono-, di-, tri- or tetra-methacrylate which is optionally halogenated or which optionally comprises at least one ether and/or ester and/or carbonate and/or carbamate and/or thiocarbamate and/or urea and/or amide group,
a polystyrene, polyether, polyester, polycarbonate, polycarbamate, polyepoxide, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate, or polyvinylbutyral,
a (co)polymer obtained from a difunctional monomer of the following formula:

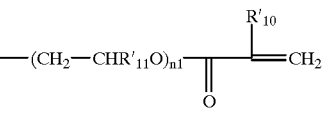

in which:
  $R_{10}$, $R'_{10}$, $R_{11}$ and $R'_{11}$ are identical or different and independently are a hydrogen or a methyl group,
  $m_1$ and $n_1$ independently are integers between 0 and 4 inclusive,
  X and X', which are identical or different, are a halogen, and
  $p_1$ and $q_1$ independently are integers between 0 and 4 inclusive;
a copolymer of at least two types of copolymerizable monomers selected from the monomers which are precursors of the polymers listed above; and
combinations thereof.

14. A (co)polymer matrix which comprises:
  at least one (co)polymer and/or reticulate according to claim 7.

15. A (co)polymer matrix according to claim 14, wherein the (co)polymer is selected from the group consisting of:
  an alkyl, cycloalkyl, (poly or oligo)ethylene glycol, aryl or arylalkyl mono-, di-, tri-, or tetra-acrylate or mono-, di-, tri- or tetra-methacrylate which is optionally halogenated or which optionally comprises at least one ether and/or ester and/or carbonate and/or carbamate and/or thiocarbamate and/or urea and/or amide group;
  a polystyrene, polyether, polyester, polycarbonate, polycarbamate, polyepoxide, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate, or polyvinylbutyral;
  a (co)polymer obtained from a difunctional monomer of the following formula:

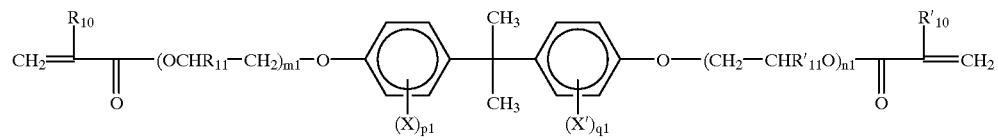

in which:
  $R_{10}$, $R'_{10}$, $R_{11}$ and $R'_{11}$ are identical or different and independently are a hydrogen or a methyl group,
  $m_1$ and $n_1$ independently are integers between 0 and 4 inclusive,
  X and X', which are identical or different, are a halogen, and
  $p_1$ and $q_1$ independently are integers between 0 and 4 inclusive;
a copolymer of at least two types of copolymerizable monomers selected from the monomers which are precursors of the polymers listed above; and
combinations thereof.

16. An ophthalmic or solar article comprising:
  at least one compound according to claim 1.

17. An article according to claim 16, wherein said article is selected from the group consisting of a lens, a glazing, and an optical device.

18. An ophthalmic or solar article comprising:
  at least one at least one photochromic composition according to claim 9.

19. An article according to claim 18, wherein said article is selected from the group consisting of a lens, a glazing, and an optical device.

20. An ophthalmic or solar article comprising:
  at least one (co)polymer and/or reticulate according to claim 7.

21. An article according to claim 20, wherein said article is selected from the group consisting of a lens, a glazing, and an optical device.

22. An ophthalmic or solar article comprising:

at least one matrix according to claim 10.

23. An article according to claim 22, wherein said article is selected from the group consisting of a lens, a glazing, and an optical device.

24. An ophthalmic or solar article comprising:

at least one matrix according to claim 12.

25. An article according to claim 24, wherein said article is selected from the group consisting of a lens, a glazing, and an optical device.

26. An ophthalmic or solar article comprising:

at least one matrix according to claim 14.

27. An article according to claim 26, wherein said article is selected from the group consisting of a lens, a glazing, and an optical device.

* * * * *